(12) United States Patent
Waterford

(10) Patent No.: US 11,554,276 B2
(45) Date of Patent: Jan. 17, 2023

(54) FACEMASK WITH FACIAL SEAL AND SEAL TEST DEVICE

(71) Applicant: Octo Safety Devices, LLC, Miami, FL (US)

(72) Inventor: Steve Waterford, Deerfield Beach, FL (US)

(73) Assignee: Octo Safety Devices, LLC, Miami, FL (US)

( * ) Notice: Subject to any disclaimer, the term of this patent is extended or adjusted under 35 U.S.C. 154(b) by 929 days.

(21) Appl. No.: 16/381,655

(22) Filed: Apr. 11, 2019

(65) Prior Publication Data

US 2020/0030562 A1 Jan. 30, 2020

Related U.S. Application Data

(60) Provisional application No. 62/656,224, filed on Apr. 11, 2018.

(51) Int. Cl.
| | | |
|---|---|---|
| A62B 27/00 | (2006.01) | |
| A61M 16/06 | (2006.01) | |
| A62B 18/02 | (2006.01) | |
| A62B 18/08 | (2006.01) | |

(52) U.S. Cl.
CPC ......... *A62B 27/00* (2013.01); *A61M 16/0616* (2014.02); *A62B 18/025* (2013.01); *A62B 18/08* (2013.01); *A61M 2205/11* (2013.01); *A61M 2205/15* (2013.01); *A61M 2210/0606* (2013.01)

(58) Field of Classification Search
CPC .............. A61M 16/06; A61M 16/0605; A61M 16/0616; A61M 16/0622; A61M 2016/0661; A61M 2205/0266; A61M 2205/0272; A61M 2205/15; A61M 2205/70; A61M 2205/705; A61M 2209/02; A61M 2210/0606; A62B 7/00;
(Continued)

(56) References Cited

U.S. PATENT DOCUMENTS

| | | | |
|---|---|---|---|
| 2,071,806 | A | 4/1936 | Walker |
| 2,067,026 | A | 1/1937 | Schwartz |
| 2,199,230 | A | 4/1940 | Schwartz |

(Continued)

FOREIGN PATENT DOCUMENTS

| | | |
|---|---|---|
| CA | 1123705 A | 5/1982 |
| CN | 111387603 A | 7/2020 |

(Continued)

OTHER PUBLICATIONS

Invitation to Pay Additional Fees dated Jan. 5, 2015 in connection with PCT/US2014/054163.
(Continued)

*Primary Examiner* — Colin W Stuart
(74) *Attorney, Agent, or Firm* — Cook Alex Ltd.

(57) ABSTRACT

A facemask configured to be used by multiple sized/shaped heads can include a primary, a secondary and a tertiary seal. In some embodiments, the primary seal is contact with the nose and cheek regions; the secondary seal is in contact with the chin region; and the tertiary seal is in contact with the cheek and chin regions. In some embodiments, the tertiary seal extends inwardly and outwardly when applied to the face. In some embodiments, the mask includes test scissors.

17 Claims, 11 Drawing Sheets

(58) Field of Classification Search
CPC ....... A62B 18/00; A62B 18/02; A62B 18/025; A62B 18/08; A62B 27/00; G01M 3/00
See application file for complete search history.

(56) References Cited

U.S. PATENT DOCUMENTS

| | | | |
|---|---|---|---|
| 2,201,315 | A | 5/1940 | Lehmberg |
| 2,410,454 | A | 11/1946 | Motsinger |
| 2,540,567 | A | 2/1951 | Bennett |
| 2,655,656 | A | 10/1953 | Moeller |
| 2,738,788 | A | 3/1956 | Matheson |
| 2,845,927 | A | 8/1958 | Hill |
| 2,964,038 | A | 12/1960 | Silverman |
| 2,983,271 | A | 5/1961 | Beck |
| 3,029,812 | A | 4/1962 | Matheson |
| 3,130,722 | A | 4/1964 | Dempsey et al. |
| 3,137,296 | A | 6/1964 | Gurtowski |
| 3,152,588 | A | 10/1964 | Rogowski |
| 3,154,073 | A | 10/1964 | Klinger |
| 3,276,445 | A | 10/1966 | Langdon |
| 3,308,816 | A | 3/1967 | Franklin et al. |
| 4,062,357 | A | 12/1977 | Laerdal |
| 4,296,746 | A | 10/1981 | Mason, Jr. et al. |
| 4,630,604 | A | 12/1986 | Montesi |
| 4,653,124 | A | 3/1987 | McNeal et al. |
| 4,688,567 | A | 8/1987 | Kikuchi et al. |
| 4,850,110 | A * | 7/1989 | Meier, Jr. ................ B26B 13/24 30/233 |
| 4,873,972 | A * | 10/1989 | Magidson ............ A62B 18/025 128/206.15 |
| 4,976,857 | A | 12/1990 | Solomon |
| 5,148,550 | A | 9/1992 | Hodgkinson et al. |
| 5,191,882 | A | 3/1993 | Vogliano |
| 5,313,935 | A | 5/1994 | Kortenbach et al. |
| 5,320,096 | A | 6/1994 | Hans |
| 5,353,789 | A | 10/1994 | Schlobohm |
| 5,357,678 | A * | 10/1994 | Wei ....................... B26B 13/005 30/162 |
| 5,357,947 | A | 10/1994 | Adler |
| 5,359,993 | A | 11/1994 | Slater et al. |
| 5,427,092 | A | 6/1995 | Shiao |
| 5,452,335 | A | 9/1995 | Slater et al. |
| 5,584,078 | A | 12/1996 | Saboory |
| 5,647,356 | A * | 7/1997 | Osendorf ................ A62B 27/00 128/206.17 |
| 5,682,879 | A | 11/1997 | Bowers |
| 6,119,694 | A | 9/2000 | Correa et al. |
| 6,161,540 | A | 12/2000 | Fecteau |
| 6,338,340 | B1 | 1/2002 | Finch et al. |
| 6,378,906 | B1 | 4/2002 | Pennaz |
| 6,691,314 | B1 | 2/2004 | Grilliot et al. |
| 6,736,085 | B1 | 5/2004 | Esnouf |
| 6,981,503 | B1 | 1/2006 | Shapiro |
| 7,311,764 | B2 | 12/2007 | Friday et al. |
| 7,540,039 | B2 | 6/2009 | Reaux |
| 7,686,018 | B2 | 3/2010 | Cerbini |
| 8,443,806 | B2 * | 5/2013 | Morelli ................... A62B 27/00 128/207.12 |
| 9,457,207 | B2 | 10/2016 | Waterford |
| 10,843,015 | B2 * | 11/2020 | Patil ....................... A62B 18/08 |
| 2003/0178026 | A1 | 9/2003 | Byram |
| 2004/0216745 | A1 | 11/2004 | Yuen et al. |
| 2005/0056286 | A1 | 3/2005 | Huddart et al. |
| 2006/0201511 | A1 | 9/2006 | Freriks et al. |
| 2007/0175480 | A1 | 8/2007 | Gradon et al. |
| 2008/0223370 | A1 | 9/2008 | Kim |
| 2008/0295843 | A1 | 12/2008 | Haas |
| 2009/0114228 | A1 | 5/2009 | Kirschner |
| 2009/0151733 | A1 | 6/2009 | Welchel et al. |
| 2009/0151734 | A1 | 6/2009 | Park |
| 2010/0126504 | A1 | 5/2010 | Johnstone |
| 2010/0153023 | A1 | 6/2010 | Parham et al. |
| 2010/0268131 | A1 | 10/2010 | Efthimiou |
| 2010/0307503 | A1 | 12/2010 | Iwamoto et al. |
| 2011/0227700 | A1 | 9/2011 | Hamerly et al. |
| 2011/0308524 | A1 | 12/2011 | Brey et al. |
| 2012/0055815 | A1 | 3/2012 | Truex et al. |
| 2012/0067349 | A1 | 3/2012 | Barlow et al. |
| 2012/0125341 | A1 | 5/2012 | Gebrewold et al. |
| 2012/0132209 | A1 | 5/2012 | Rummery et al. |
| 2012/0325221 | A1 | 12/2012 | Tran |
| 2013/0074845 | A1 | 3/2013 | Smith et al. |
| 2014/0026897 | A1 | 1/2014 | Saroch et al. |
| 2014/0216474 | A1 | 8/2014 | Mittelstadt et al. |
| 2015/0107596 | A1 * | 4/2015 | Mashiko ................ A62B 18/08 128/206.15 |
| 2015/0151147 | A1 | 6/2015 | Fun |
| 2015/0314148 | A1 | 11/2015 | Waterford |
| 2016/0001102 | A1 | 1/2016 | Huh |
| 2016/0166859 | A1 | 6/2016 | Rachapudi et al. |
| 2016/0271428 | A1 | 9/2016 | Ehler et al. |
| 2016/0317848 | A1 | 11/2016 | Zilberstein et al. |
| 2017/0106217 | A1 | 4/2017 | Kuhn |
| 2017/0109943 | A1 | 4/2017 | Sutton et al. |
| 2017/0128753 | A1 | 5/2017 | Waterford |
| 2017/0312555 | A1 | 11/2017 | Olmsted et al. |
| 2017/0368381 | A1 | 12/2017 | Awiszus et al. |
| 2017/0372216 | A1 | 12/2017 | Awiszus et al. |
| 2018/0250537 | A1 | 9/2018 | Waterford |
| 2018/0280738 | A1 | 10/2018 | Gabriel |
| 2018/0369529 | A1 | 12/2018 | Grashow et al. |
| 2019/0125011 | A1 | 5/2019 | Eisenbrey et al. |
| 2020/0114178 | A1 | 4/2020 | Waterford et al. |

FOREIGN PATENT DOCUMENTS

| | | |
|---|---|---|
| JP | 22020-059954 A | 4/2020 |
| JP | R22020-059954 A | 4/2020 |
| KR | 1020190097802 A | 8/2019 |
| KR | 102080754 B1 | 4/2020 |
| KR | 10-2110687 B1 | 5/2020 |
| WO | 2002024279 A1 | 3/2002 |
| WO | WO 2002024279 A1 | 3/2002 |
| WO | 2013027174 A1 | 2/2013 |
| WO | WO 2013027174 A1 | 2/2013 |
| WO | 2013094806 A1 | 6/2013 |
| WO | WO 2013094806 A1 | 6/2013 |
| WO | 2015035101 A2 | 3/2015 |
| WO | WO 2015035101 A2 | 3/2015 |

OTHER PUBLICATIONS

International Search Report and Written Opinion dated Apr. 22, 2015 in connection with PCT/US2014/054163.
International Preliminary Report on Patentability dated Mar. 17, 2016 in connection with PCT/US2014/054163.
International Search Report and Written Opinion dated Oct. 25, 2016 in connection with PCT/US2016/042594.
International Preliminary Report on Patentability dated Jan. 25, 2018 in connection with PCT/US2016/042594.
U.S. Appl. No. 15/911,109, filed Mar. 3, 2018, Office Action dated Apr. 27, 2021.
U.S. Appl. No. 16/593,851, filed Oct. 4, 2019, Office Action dated Dec. 24, 2021.
PCT/US2014/054163 filed on Sep. 4, 2014, Invitation to Pay Additional Fees dated Jan. 5, 2015, International Search Report and Written Opinion dated Apr. 22, 2015, International Preliminary Report on Patentability dated Mar. 17, 2016.
U.S. Appl. No. 14/477,840, filed Sep. 4, 2014, Office Action dated Jan. 16, 2015.
U.S. Appl. No. 14/801,808, filed Jul. 16, 2015, Office Action dated Nov. 19, 2015, Notice of Allowance dated Jun. 9, 2016.
U.S. Appl. No. 15/226,877, filed Aug. 2, 2016, Office Action dated Nov. 1, 2017, Office Action dated Jun. 13, 2018, Office Action dated Dec. 13, 2018, Office Action dated Apr. 4, 2019.
PCT/US2016/042594 filed on Jul. 15, 2016, International Search Report and Written Opinion dated Oct. 25, 2016, International Preliminary Report on Patentability dated Jan. 25, 2018.
International Search Report and Written Opinion dated Jul. 19, 2022, in connection with PCT/US2022/023875.

(56) References Cited

OTHER PUBLICATIONS

U.S. Appl. No. 15/911,109, filed Mar. 3, 2018, Office Action dated May 10, 2022.
U.S. Appl. No. 16/593,851, filed Oct. 4, 2019, Notice of Allowance dated Apr. 19, 2022.
PCT/US2022/023875 filed on Apr. 7, 2022, International Search Report and Written Opinion dated Jul. 19, 2022.

* cited by examiner

FACEMASK WITH FACIAL SEAL AND SEAL TEST DEVICE

CROSS-REFERENCE TO RELATED APPLICATIONS

This application claims priority to U.S. Provisional Patent Application Ser. No. 62/656,224 filed on Apr. 11, 2018 entitled "Facemask with Facial Seal, Eye Shield and Strap Adjustment Assembly and Seal Test Device". The '224 application is hereby incorporated by reference in its entirety.

FIELD OF THE INVENTION

The present invention concerns facemasks, and in particular facemasks and eye shields to protect against airborne particulates and pathogens.

Masks are often used as a form of protection against airborne particulates and pathogens, including bacteria and viruses. Facemasks are typically worn over the mouth and nose of the wearer and can incorporate a form of eye protection. Masks can be used in environments with high levels of airborne particulates and/or allergens where the wearer wishes to not inhale said particulates. To effectively reduce a wearer's exposure to airborne substances, a respiratory protection device needs to fit well and effectively filter out said substances.

Preventing inhalation and contact with airborne pathogens and environmental allergens is not only important in environments that require high levels of air purity, such as hospitals, but also in homes of people suffering from allergies. Additionally, wearers suffering from respiratory infections can benefit from the filter capture of pathogens and allergens when out in public.

One issue when attempting to manufacture a standard facemask is accommodating the various sizes/shapes of potential wearers. Traditionally this issue has been overcome by manufacturing masks of several sizes and/or shapes.

However, this method is not ideal as the lack of a single mask designed for various head shapes/sizes requires additional planning, preparation, purchasing, storing and supplying different sized respirators. This is especially problematic when masks are to be used in emergency situations.

In addition, traditionally mask wearers must choose a correctly sized mask to fit their facial characteristics. Not only does this cost time, but often the wearer chooses the wrong sized/shaped mask for his/her face. The resulting improper fit can prevent the mask from properly sealing against the wear's face and properly filtering airborne contaminants, particles and/or pathogens. Often the user is unaware that the mask does not fit. Again, this is especially concerning during emergency situations.

Existing respirator head attachment systems range from simple, non-adjustable elastic bands that fit behind a wearer's ears to complex head harness assemblies. Respirators employing non-adjustable elastic band head attachment provide subpar facial coverage as the straps and mask cannot be adjusted to different tensions to provide customized, comfortable coverage to different facial contours. Head harness assemblies are often uncomfortable to wear and difficult to adjust with numerous buckles, fasteners and straps.

Adjustable assemblies that utilize two sets of upper and lower straps that meet behind the head require each strap be singularly adjusted to center the mask on the face.

What is needed is a single mask design capable of effectively working with various head shapes/sizes. In at least some embodiments, the mask should work with the five certification head forms of the National Institute of Occupational Safety and Health (NIOSH).

In addition to providing a mask design capable of effectively working with various head shapes/sizes, there is a need for improvement in testing the seal of various masks.

In some embodiments it would be helpful to have a mask system with an adjustable elastic mask strap system that can work without hardware components. In some embodiments, the system could self-center on the head and face of a user and be adjusted by the wearer via a single, simple process. In most embodiments, the mask system would alleviate discomfort mask wearers often encounter (particularly over their ears).

Traditionally seal tests involve placing the wearer inside an up-side-down tube, sealed at the top, wherein a noxious odor is introduced. If the wearer can smell the odor, then the seal is insufficient, and adjustments are made. The test is then repeated until a successful seal has been achieved. This testing is time consuming. In addition, even after a proper seal is made, the seal may be broken, unknown to the wearer, during use. Improvements to testing the seal of mask are needed.

Additionally, there is a need for an improved eye shield that can easily integrated to a mask system. Independent conventional eye shields suffer from inherent flaws including the use of multiple straps to maintain position. These straps can come undone potentially resulting in contamination of the wearer. These straps can also lead to difficulty of maintaining the eye shield's original position, place the shield against the forehead and other vulnerable areas, and/or interconnect with facemasks providing continuity of protection between the two.

SUMMARY OF THE INVENTION

The embodiments described below and shown in the various drawings overcome many known shortcomings of conventional facemasks and eye shields.

Such shortcomings of conventional facemasks include a lack of adjustability and perpetuation of restricted and/or misdirected air-flow, imperfect sealing, and the inability for a single mask to protect wearers of different sizes and shapes.

In some embodiments, the masks provide, among other things, a continuous strap system. In some of these embodiments, the strap is integrated directly into an opening that enables it to be snapped into an area in front of the nose of the wearer of the mask, generating forces with components parallel and perpendicular to the plane of the face. In some embodiments, the mask can be configured to pull upward and backwards beneath the chin as well as towards the plane of the face to provide a tight fit.

In some embodiments, the mask assembly can comprise a lower air intake. In certain embodiments, this intake is located on the lower front section of a mask. In some embodiments, the air intake directs airflow at a non-right angle to the plane of a filter contained within the mask.

In some embodiments, an air filter is internal to the mask. In certain embodiments, the filter is replaceable. In at least some embodiments, the filter is sealed within the mask structure. In some embodiments, the air filters have biocidal components.

In some embodiments, there are no front-facing openings on the mask. In some of these embodiments, the mask assembly can comprise channels that direct exhaled air sideways and/or backwards, in a direction parallel to and/or behind the plane of a wearer's face. In some embodiments, this venting occurs from multiple sides of a mask simultaneously. In at least some of these embodiments, vent systems are symmetrically placed about an axis in the plane of the mask. In certain embodiments, the exhaled air is directed towards the cheeks, neck and/or ears of a wearer.

In some of the embodiments, air is blocked by a solid front-facing construct that restricts direct access to an internal filter from frontal air flow. In at least some of these embodiments, the exhaled air flows through channels backwards and/or sideways from the mask.

In some embodiments, the mask assembly can comprise a nose clip and/or elastic components to complete a continuous strap. In some embodiments, the strap can clip or snap into a mask. In some embodiments, the continuous strap can clip or snap into a component that allows for strap tension adjustment.

In some embodiments, openings in a mask assembly can be circular, oblate, and/or polygonal. In some embodiments, openings can form to receive various attachments. In certain embodiments, a mask assembly can comprise extrusions along an interior rim and/or on a top or bottom section of the mask.

In certain embodiments, a mask assembly can comprise an eye shield assembly. In some of these embodiments, the eye shield is transparent. In some embodiments, an eye shield can comprise at least one extrusion inserted through a pair of through holes. In certain embodiments, a shield can be secured at the nose area of the mask. In some embodiments, eye shield can also rest against the wearer's forehead and/or cheekbones.

Some embodiments of the mask assembly occur at least in part in the following configuration:
  (a) at least one air vent for bidirectional flow of air being inhaled and exhaled by the wearer, the at least one airflow intake capable of directing inward airflow to strike an interior air filter at an oblique angle;
  (b) a head mounting pad having a single or dual pull to tension the mask assembly against the wearer's face; and
  (c) a continuous strap positionable under the chin of the wearer and in the nose area.

In some embodiments, a mask has snap-in receivers. Some embodiments of snap-in receivers are given in the figures presented herein, however these are not meant to be the only disclosed locations or embodiments of snap-in receivers.

In embodiments having snap-in receivers, the receivers are often (but not exclusively) meant to receive strap(s) for the mask assembly. In some embodiments, the receivers are designed to accommodate a single, continuous strap. In some embodiments, a mask has two snap-in receivers, one in the nose area, and one in the proximity of a wear's chin. These receivers need not be similarly designed to one another. For instance, one receiver can resemble a slot in the mask itself, while the other receiver can resemble a hook. In some embodiments, snap-in receivers can accommodate other mask attachments, such as an eye shield assembly.

In some embodiments, the continuous strap is elastic, and can be adjusted by equally tensioning the strap mounted within a strap adjustment component at the back of the head. In at least some embodiments, such a design provides numerous advantages over existing masks, such as fewer breakable components, removing the need for clasps or buckles, increased ability to adjust applications of force by the mask to conform to various faces, and ease of mask removal.

In some embodiments, there is a broadly adaptive mask assembly containing a primary seal, a secondary seal and a tertiary seal. In at least some embodiments, the adaptive mask assembly is a single mask that is broadly adaptive to multiple shapes and sizes of different users.

In some embodiments, the primary seal encompasses the surface of the perimeter of the mask and is substantially in contact with the nose and cheek regions of a wearer's face. In some embodiments, the secondary seal encompasses a surface of the perimeter of the mask and is substantially in contact with the chin region of a wearer's face. In some embodiments, the tertiary seal is disposed about the inner surface of the perimeter of the mask and is substantially in contact with the cheek and chin regions of the wearers face.

In at least some embodiments, the tertiary seal is attached to the primary seal and extends outwardly.

In some embodiments, the tertiary seal is configured to encompass the secondary seal including a chin cup providing a double seal.

In some embodiments, the tertiary seal extends outwardly from the surface of the primary seal, wherein, in some embodiments, the tertiary seal is configured to form an internal and external lip when compressed against a user's face expanding the surface area and forming a better seal.

In certain embodiments, the mask can include crossbars formed within upper vents of the mask to accept attachment elements of a shield assembly.

In at least some embodiments, a seal test scissor assembly for passive testing of a mask assembly can include the following configuration:
  (a) a first scissor frame and second scissor frame in a substantially cross-shaped configuration and attached by a fulcrum point that is subsequently biased into open and closed positions to mount the mask;
  (b) attachment points on the scissor frames to cooperate with a biasing mechanism to clamp around a mask;
  (c) a sealing material is at least partially disposed about the first scissor frame and second scissor frame; and
  (d) seal test scissors constructed to be biased in a closed position.

In certain embodiments, a shield assembly can include features including a shield including a headband conforming against the face and attached by clip-on elements. In some embodiments, the clip-on element can also have an adjustable element for biasing of a shield against a user's face. In at least some embodiments, the shield is capable of being attached to a respiratory mask in order to protect the face and/or eyes of a wearer.

In some embodiments, a shield is used in conjunction with a respiratory mask by way of the clip-on elements to provide protection from airborne contaminants, particles and/or pathogens.

In some embodiments, a mask can be secured to the face of a wearer by a strap adjustment assembly. In certain embodiments, the strap adjustment assembly can include a frame that has a strap bonded to it and which then loops back into said frame. In some embodiments, once the strap is looped within the adjustment frame it can be manually adjusted to different tension settings to alter the tension of the straps to accommodate a wide variety of head sizes and facial contours. In some embodiments, tension settings can be retained within the adjustment frame.

DETAILED DESCRIPTION OF ILLUSTRATIVE EMBODIMENT(S)

Mask Assembly Configured to Fit Multiple Face Sizes and Shapes

Figure 1:
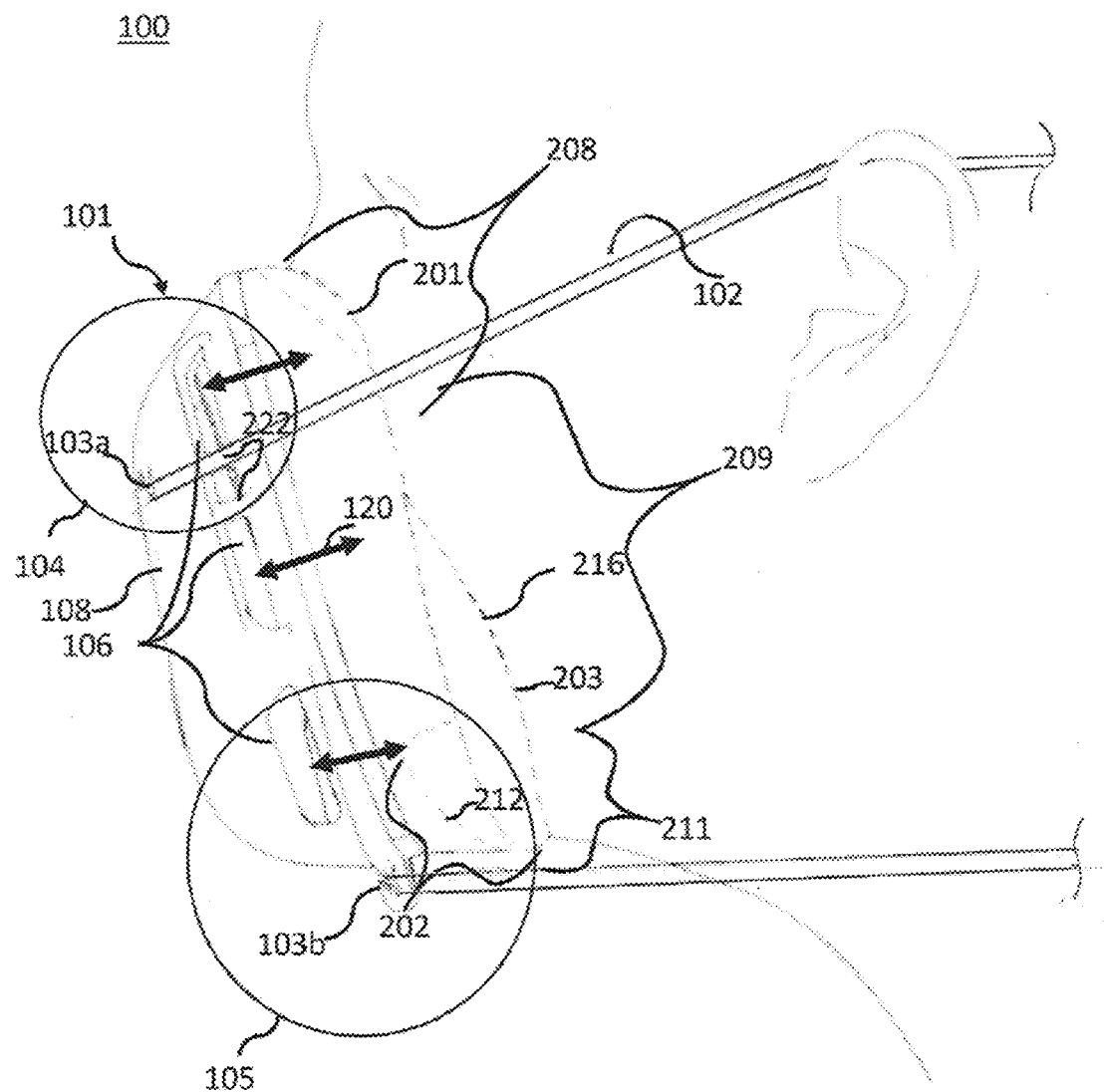
FIG. 1 is a cutaway side view of a mask assembly configured to fit multiple face sizes and shapes illustrating a primary seal, a secondary seal, and a tertiary seal.

FIG. 1 is a side view of mask assembly 100. In some embodiments, mask assembly 100 can have continuous strap 102. Strap 102 can be made of, among other things, various straps 102, cords, tubing, and/or O-ring stock. In most, if not all, embodiments, strap 102 is elastic.

In the illustrated embodiment, snap-in receivers 103a and 103b are present in nasal area 104 of mask 101 and beneath chin area 105. Snap-in receiver 103b, located beneath the chin, resembles a hook receiving continuous strap 102. Snap-in receiver 103a, located in the nasal section, shows a valley defined by two extrusions that receives the upper part of continuous strap 102. In addition to hooks and extrusions, snap-in receivers 103a and 103b can resemble, among other things, voids, divets, sets of ridges, and other suitable moldings of mask 101 that can accommodate straps 102.

In many embodiments, snap-in receivers offer several advantages, such as allowing a wearer to replace strap 102 on the fly. For example, if strap 102 were to break and a wearer did not have access to a proper replacement strap 102, the wearer could utilize a wide variety of suitable materials such as his or her own shoelace for an immediate field repair. This feature could be life-saving should such an immediate field repair be necessary in an infectious or hazardous air environment.

In at least some embodiments, vents 106 are configured to vent exhaled $CO_2$ and $H_2O$-laden air sideways and/or backwards towards a wearer's face and neck. In some embodiments, vents 106 do not allow exhaled air to be channeled downward. In some embodiments, this is accomplished via flaps that impede the flow of are in the downward direction. In some embodiments, vents have lips configured to direct the flow of exhaled air.

In some embodiments, mask 101 contains primary seal/facial skirt 201. In some embodiments, primary seal 201 has elastic properties. In at least some embodiments, primary seal 201 can be made of a soft silicone and/or other materials that conform to a wearer's face and/or materials capable of creating an airtight seal.

In at least some embodiments, front section 108 of mask 101 is constructed of a hard plastic. In other embodiments, other materials, including but not limited to rubber, silicone, metals, other thin plastics or composite materials can be used to construct front section 108. In certain embodiments, front section 108 has unrestricted venting that is large enough to improve the speech clarity of a wearer when compared to traditional masks.

In at least some embodiments, strap 102 self-aligns within snap-in receiver 103a and snap-in receiver 103b and crosses behind the head to produce a snug, self-centering fit.

In some embodiments, mask assembly 100 can utilize two straps 102, a top strap configured to slide into the snap-in receiver 103a which allows the top strap to slide back and forth to balance the position of clips and/or buckles and a bottom strap configured to slide in snap-in receiver 103b. In some embodiments, snap-in receivers allow at least one, if not both of straps 102 to be easily removed. In some embodiments, clips and/or buckles can be used to help stabilize the upper and/or lower straps 102. Various embodiments of straps 102 can be configured to fit with a mask design given the placement of various snap voids or receivers. In some embodiments, open-ended straps 102 can be tied behind the ears and/or the head and/or secured and adjusted.

Existing elastomeric half-face masks use one-way check valves, generally elastic diaphragms mounted directly in front of the mouth, to enable exhalations to vent. Inhalations and exhalations are each mono-directional. Exhaled air above the exhaust vent is thus trapped above it, which prevents nasal breathing primarily due to the build-up of $CO_2$. In addition, particulates and/or pathogens captured by the filter material migrate through that filter material with every inhalation as the exhalation, which pushes them outwards, goes out thru the diaphragm vent.

In some embodiments, mask assembly 100 is configured to reduce, if not completely prevent, forward facing air inhalations and exhalations. In some embodiments, vents 106 can be channeled to create oblique airflow patterns over a filter insert. In certain embodiments having pleated filter insert(s), these channels can be configured to coincide with filter pleats.

In FIG. 1, there is no direct access to an internal filter from the frontal flow of air on to the mask surface, and the exhaled air is vented sideways and/or backwards relative to the plane of a wearer's face through vents 106. In some preferred embodiments, vents are arranged symmetrically around mask 101.

In some embodiments, vents 106 are configured to allow the escape of exhaled heat, moisture and/or $CO_2$. In certain embodiments, vents 106 are sufficiently large enough such that a wearer can be heard more clearly. In some embodiments, vents 106 force exhaled air and/or $CO_2$ off to the sides of a wearer's face. In some embodiments, this is accomplished by placing vents 106 near the upper most sides of mask 101 where exhaled air tends to migrate. The sideways and backwards venting of exhalations is of particular importance when the wearer of a mask is ill to protect those in front. Vents can be configured to aid in reducing, if not completely eliminating, frontal contact of inhaled particles onto the filter.

In some embodiments, vents 106 placed above the nostrils of the wearer support improved nasal breathability over conventional masks and respirators and accentuates the oblique angle air flow that supports greater capture of air-borne elements within the surface of the filter.

In some embodiments, the bi-directional airflow design of the presently disclosed mask, reduces the likelihood of particulates and/or pathogens migrating through the filter. In at least some embodiments, no air can be trapped within the mask as the uppermost vents are above the wearers' nostrils.

FIG. 1 shows air vents 106, along with the inward and rearward flow of air shown in arrows 120. In FIG. 1, primary seal 201 is shown. In some embodiments, primary seal 201 has elastic properties to conform to the face of the wearer.

In at least some embodiments, sections of mask 101 are coated with silicone, rubber, and/or other comfort inducing materials. In at least some embodiments, these materials can help a user wear a mask for long period without discomfort and/or worrying about transmission/reception of infections.

In some embodiments, mask assembly 100 can be boiled/autoclaved and is reusable. In some embodiments, mask assembly 100 can be cleaned by chemical disinfectant methods. In some embodiments, strap 102 can be boiled and/or autoclaved. In certain embodiments, strap 102 does not need to be disassembled from mask 101 before being boiled and/or autoclaved. In some embodiments, mask assembly 100 can be cleaned and/or boiled without disassembling it.

In at least some embodiments, mask system 100 allows for particles exhaled by a wearer to strike a pleated filter at an oblique angle. In at least some embodiments, in the event that a wearer coughs and/or sneezes and induces a high-pressure zone preceding the filter in the mask, the filter captures particles and vents air backwards away from individuals the wearer may be facing or interacting with.

In at least some embodiments, inhalation and exhalation pressures are inherently close to identical within a mask system. Such embodiments offer advantages such as retarding the migration of particulates and/or pathogens through a filter system.

In at least some embodiments, mask assembly 100 is configured to be used with at least the five National Institute for Occupational Safety and Health (NIOSH) certification adult head forms; small, short-wide, large, medium, long-narrow. In some embodiments, mask assembly 100 can fit a child's face.

In at least some embodiments, mask assembly 100 can accommodate different shapes and sizes of a wearers face. In some embodiments, this is accomplished with primary seal 201, secondary seal 202, tertiary seal 203 and/or a combination thereof. In some embodiments, primary seal 201, secondary seal 202 and/or tertiary seal 203 fit securely against the face of the wearer.

FIG. 1 further illustrates dotted lines, representing portions of each of the three facial seals from an internal and external perspective when mask 101 is in use.

Primary 201, secondary 202 and tertiary seals 203 are shown about the perimeter of upper nose 208 and cheek regions 209, areas parallel to mouth and cheeks and areas under chin 211. In at least some embodiments, primary seal 201 is continuous about the perimeter of mask 101. In at least some embodiments, secondary seal 202 creates chin cup 212 around chin region 211. Chin cup 212 can engage with the chin of the wearer.

In at least some embodiments, tertiary seal 203 can be intermittently continuous (not shown) or continuously positioned about the areas under chin region 211 and/or areas parallel to mouth and cheeks 209. FIG. 1 shows tertiary seal 203 from an internal and external perspective when facial mask assembly 100 is in use. The external dotted line depicts the outwardly extending tertiary seal 203 and the internal dotted line depicts tertiary seal 203 folding inward against the face of the aforementioned problem areas while in use.

In at least some embodiments, tertiary seal 203 forms external lip 216 that extends away from facial mask 101 on cheek region 209.

In at least certain embodiments, external lip 216 doubles as at least one additional seal under secondary seal 202.

Figure 2:
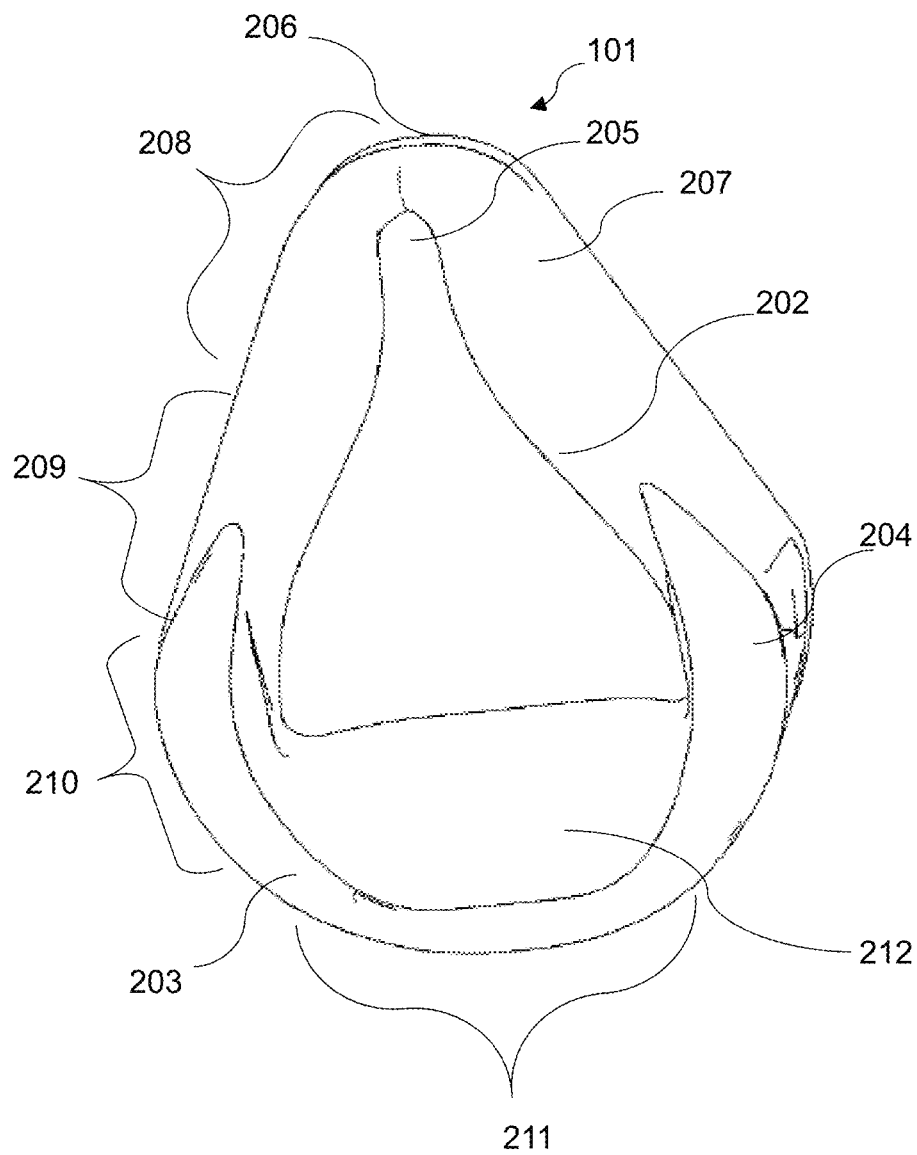
FIG. 2 is a back-perspective view of the mask of FIG. 1.

In at least some embodiments, tertiary seal 203 forms an internal lip that extends toward the mouth, such as shown in FIG. 2.

In at least certain embodiments, the internal lip doubles as at least one additional seal under secondary seal 202.

In at least some embodiments vents 106 contain dual crossbars 222 to receive at least one attachment element (not shown).

In at least some embodiments, mask assembly 100 is reusable by a wearer of mask assembly 100.

In at least some embodiments, mask assembly 100 is made in a comfortable design for short or long-term wear.

In at least some embodiments, mask assembly 100 seals by various materials and designs, including but not limited to, materials of elastomeric masks, positive airway pressure masks and designs.

FIG. 2 is a perspective view of mask is a facial surface view of at least one embodiment of mask 101 illustrating, among other things, primary seal 201 and keyhole slot 205 positioned substantially about upper nose region 208 of primary seal 201. Primary seal 201 continuous about upper nose 208 and cheek regions 209, areas parallel to mouth 210 and cheeks 209 and about areas under chin region 211. Keyhole slot 205 substantially encompasses bridge 206 and sides 207 of upper nose region 208 of primary seal 201 to provide proper placement and fit of mask 201.

In at least some embodiments, secondary seal 202 is positioned about primary seal 201 in problem areas, including but not limited to, areas parallel to mouth 210 and under chin region 211 of mask 201. Secondary seal 202 can further include chin cup 212 for increased fit, support and seal of chin region 211, and to provide a proper seal of mask 101 against a user's face.

In at least some embodiments, tertiary seal 203 is positioned about primary seal 201 in problem areas, including but not limited to, areas parallel to mouth 210 and cheeks 209. In at least some embodiments, tertiary seal 203 extends outward from primary seal 201 when at rest.

In at least some embodiments, tertiary seal 203 can inwardly fold, deform and/or flatten against the face to enable a broadly effective seal and expand the sealing area when worn. Similarly, in some embodiments tertiary seal 203 can outwardly fold, deform and/or flatten against the face to enable a broadly effective seal and expand the sealing area when worn.

Seal Test Scissors

In at least some embodiments, mask assembly 200 includes test scissors 240 for use in conjunction with facial mask 220 to confirm facial mask 220 is properly sealed. In at least some embodiments, test scissors 240 provide a passive method of testing the seals of facial mask 220 while in use.

Figure 3:
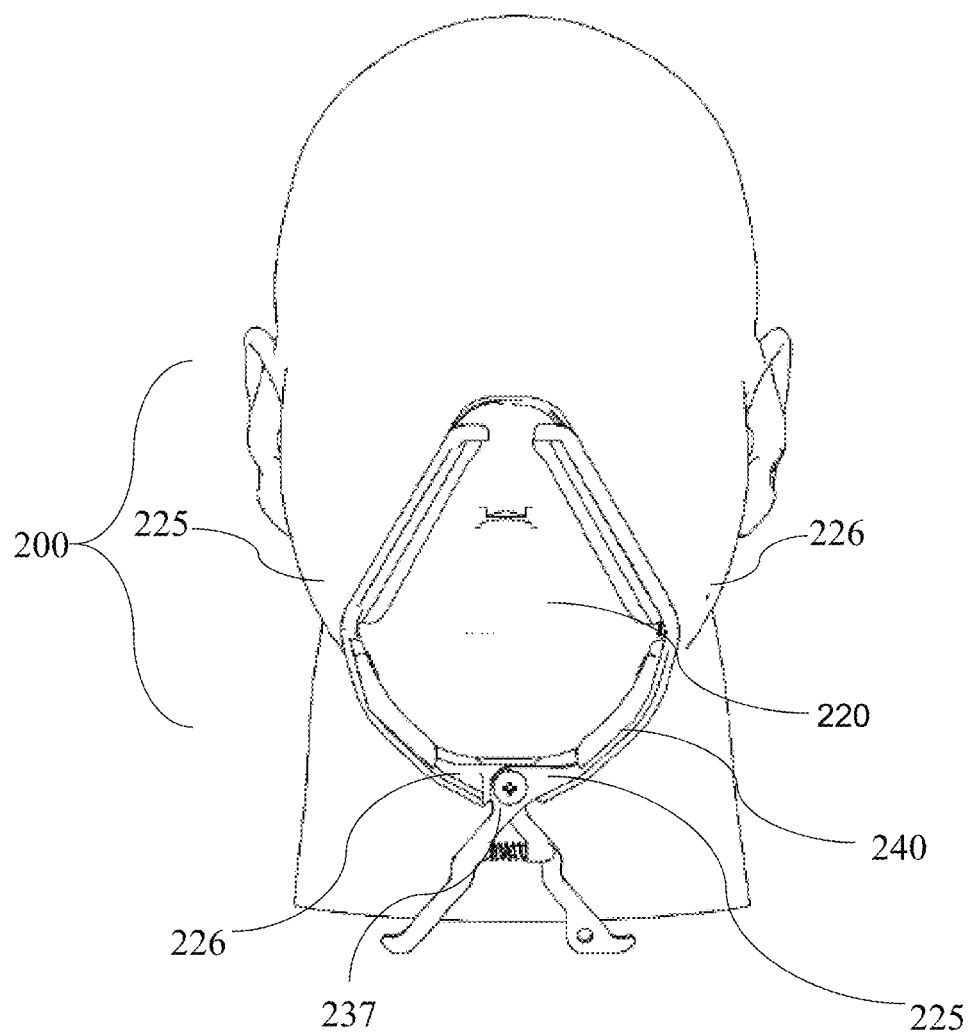
FIG. 3 is a front view of a mask assembly with test scissors.

FIG. 3 shows a frontal view of at least one embodiment of mask assembly 200 depicting test scissors 240 with straps removed for clarity. When test scissors 240 are temporarily mounted in place, test scissors 240 are substantially mounted along facial mask 220 about upper and lower side vents enabling the use of a spring-loaded mechanism 237 to bias scissor frames 225, 226 against facial mask vents. The placement of test scissors 240, allows test scissors 240 to substantially, if not entirely, seal facial mask vents. When facial mask vents are properly sealed, they prevent, or at least reduce, bidirectional airflow. This allows the user to passively test facial mask 220 seals by attempting to inhale, while facial mask vents are temporarily sealed.

In at least some embodiments, when bidirectional airflow is prevented, or at least reduced, by test scissors 240, the user inhales such that if a proper seal exists, mask 220 is at least partially pulled inward towards the face of the wearer.

In some embodiments, when the bidirectional airflow is prevented, or at least reduced, by test scissors 240, and the user is then able to inhale, such that if an improper seal exists, mask 220 will draw air through the seal. If air is drawn through a portion of the seal the user knows mask 220 is not properly sealed.

Figure 4:
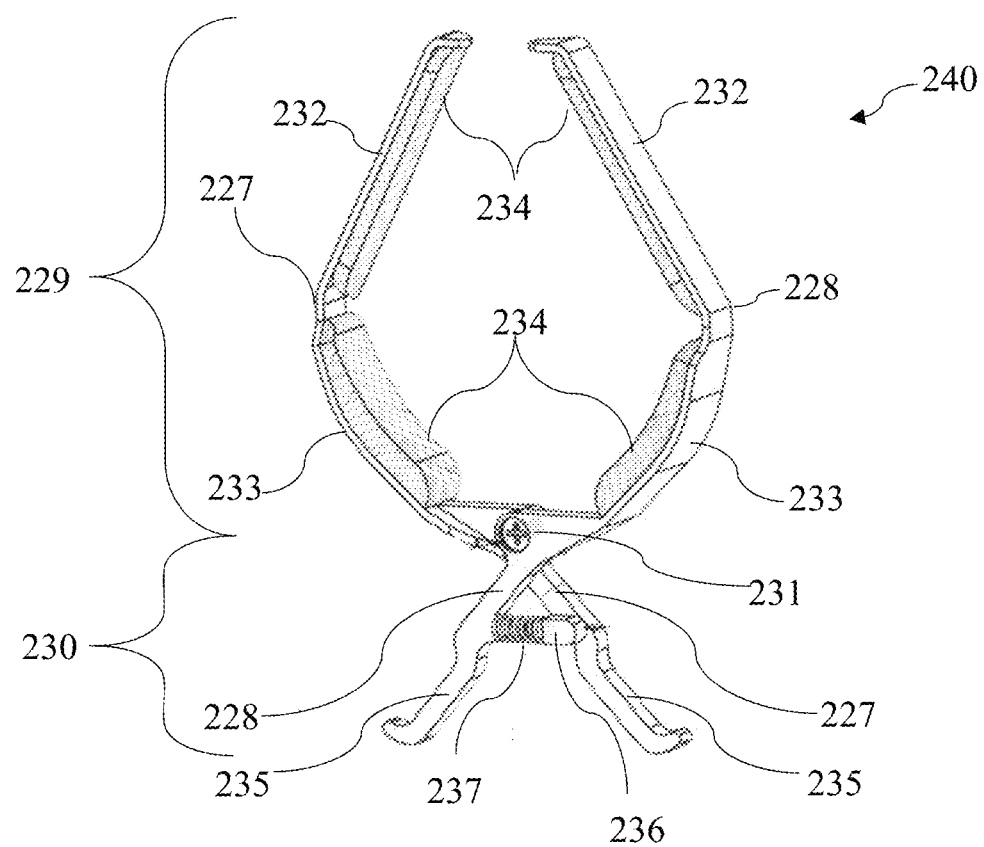
FIG. 4 is a front perspective view of a pair of test scissors in a closed position.

FIG. 4 is a frontal perspective view showing an example of test scissors 240 in a relaxed state and in a closed position. In the shown embodiments, test scissors 240 have first scissor frame 227 and second scissor frame 228, each having top portion 229 and bottom portion 230 separated by fulcrum point 231. In some embodiments, fulcrum point 231 affixes at least a portion of first scissor frame 227 and second scissor frame 228 to one another in a substantially cross-shaped manner. In at least some embodiments, fulcrum point 231 includes attachment mechanism for securing first scissor frame 227 and second scissor frame 228.

In at least some embodiments, top portion 229 of first 227 scissor frame and second scissor frame 228 have upper 232 and lower 233 portions. In at least some embodiments, upper portion 232 has an inward curvature that is substantially similar to the curvature of nose 208 and cheek 209 regions of facial mask 220. In at least some embodiments, lower portion 233 has an inward curvature that is substantially similar to the curvature parallel to the mouth 210 and chin 211 areas of the facial mask 201. In some embodiments, upper 232 and/or lower 233 portions of top portion 229 have sealing material 234, including but not limit to, elastomeric, elastic polymeric materials, open cell foam and/or closed cell foam.

In some embodiments, bottom portion 230 of first scissor frame 227 and second scissor frame 228 are configured to be handles 235, In some embodiments, at least one attachment point 236 is used for connecting biasing mechanism 237 to handles 235. In some embodiments, biasing mechanism 237 can be made of, but not limited to, springs, shape memory alloys and actuators, magnets and other biasing mechanisms.

In some embodiments, test scissors 240 are naturally biased in a closed position by biasing mechanism 237. In some embodiments, test scissors 240 can have biasing mechanism 237 in an extended state with test scissors 240 in a closed position. In some embodiments, the extended state can further bias handles 235 in an outward direction. In at least some embodiments, the extended state requires compression to bias test scissors 240 in an open position.

Figure 5:
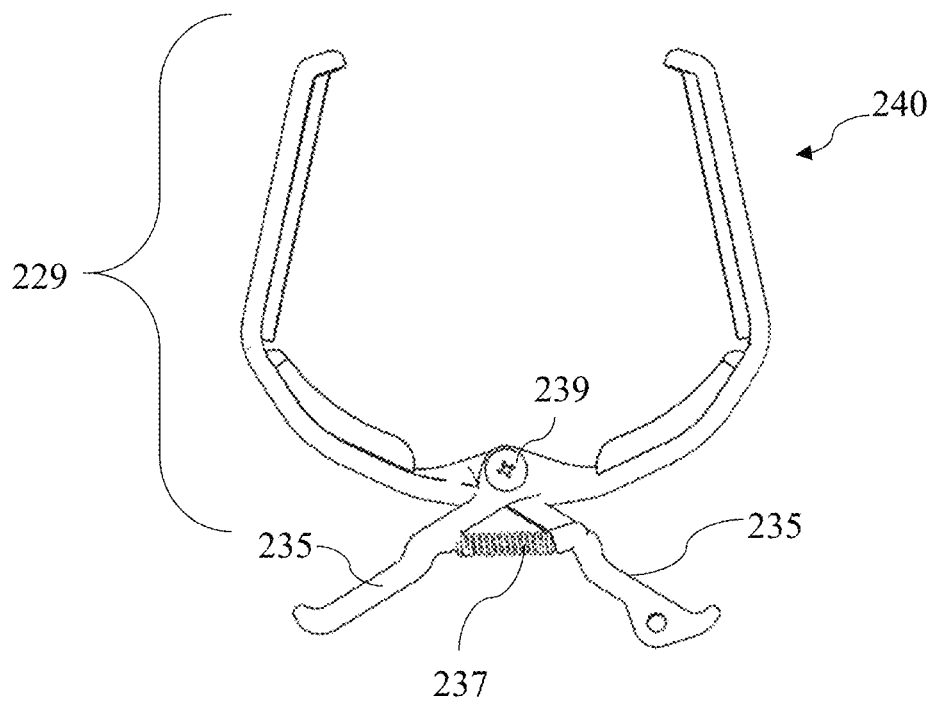
FIG. 5 is a front view of a pair of test scissors in an open position.

FIG. 5 is a front view of an embodiment of test scissors 240 in the open position. In some embodiments, biasing mechanism 237 is biased such that top portion 229 of test scissors 240 spread outwardly when handles 235 are spread outwardly by a user. In some embodiments, when handles 235 are spread outwardly, biasing mechanism 237 can be extended by the user.

In at least one embodiment, the fulcrum attachment mechanism can be a suitable method of attachment mechanism including, but not limited to, screws, rods, hinges, dowels, pins and/or pegs.

Clip-On Shield Assembly

In conjunction with facial mask assemblies, users who are concerned about airborne contaminants, particulates and/or pathogens often desire protection of the eyes. In at least some embodiments, shield 638 can provide protection for its users.

Figure 6:
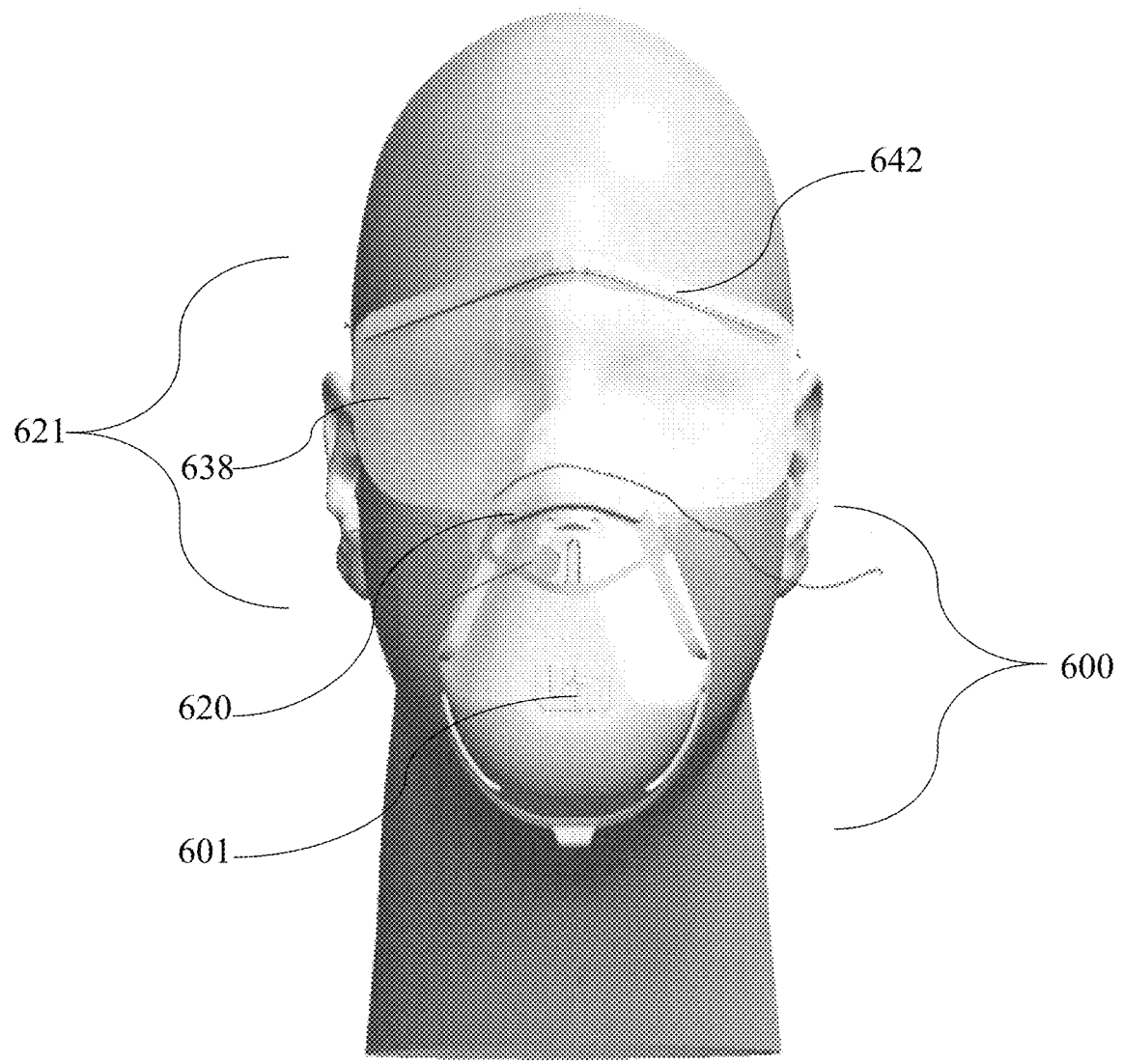
FIG. 6 is a front view of a mask assembly with an eye shield assembly.

FIG. 6 is a frontal view of an embodiment of mask assembly 600 with shield assembly 621 attached. In some embodiments, such as the one depicted in FIG. 6, shield assembly 621 is attached to mask 601 by way of clip-on element 620. In some embodiments, shield assembly 621 has at least one conformal headband 642. In certain embodiments, when shield assembly 621 is attached to mask assembly 600, shield assembly 621 biases shield 638 toward the wearer. In at least some of these embodiments, a wearer is provided with continuity of protection, as mask assembly 600 and shield assembly 621 partially overlap. This overlap provides a protective barrier from airborne particulates, fluids and/or solids.

In at least some embodiments, shield assembly 621 can be equally protective of the perimeter of shield 638 to provide additional protection.

Figure 7:
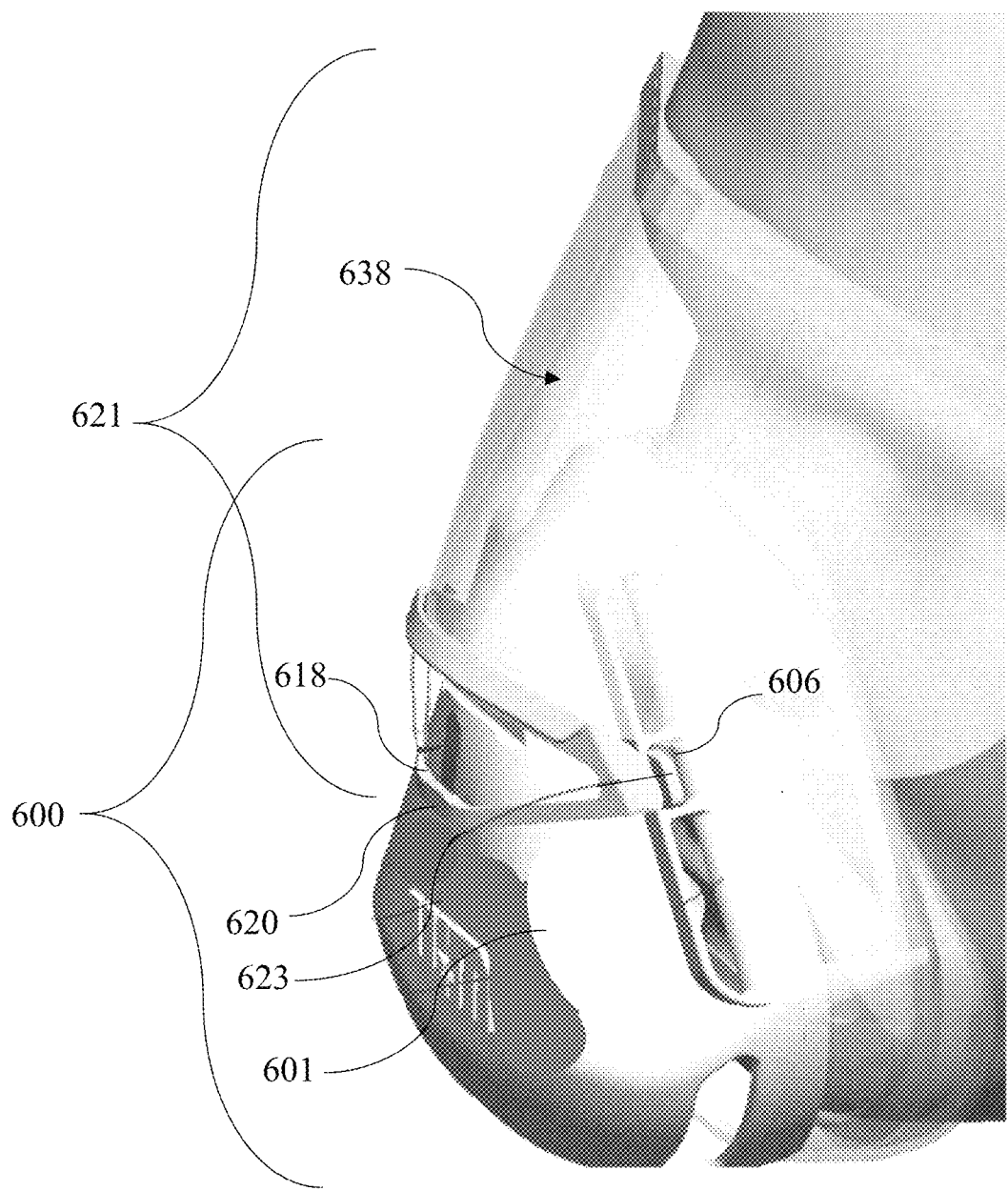
FIG. 7 is side perspective view of a mask assembly and eye shield assembly attached to the mask.

FIG. 7 is a side perspective of a certain embodiment of mask assembly 600 and shield assembly 621. In the illustrated embodiment, shield assembly 621 is attached to mask assembly 600, having shield 638 and clip-on element 620. In some embodiments, clip-on element 620 substantially conforms to the shape of mask 601 in order to facilitate attachment. In at least some embodiments, clip-on element 620 is attached to at least one upper vent 606 of mask 601 by way of attachment element 623 and includes adjustable element 619 (see FIG. 8) configured to engage opening 618 in mask 601. In at least some embodiments, adjustable element 619 is capable of biasing shield assembly 621 toward the user's face.

Figure 8:
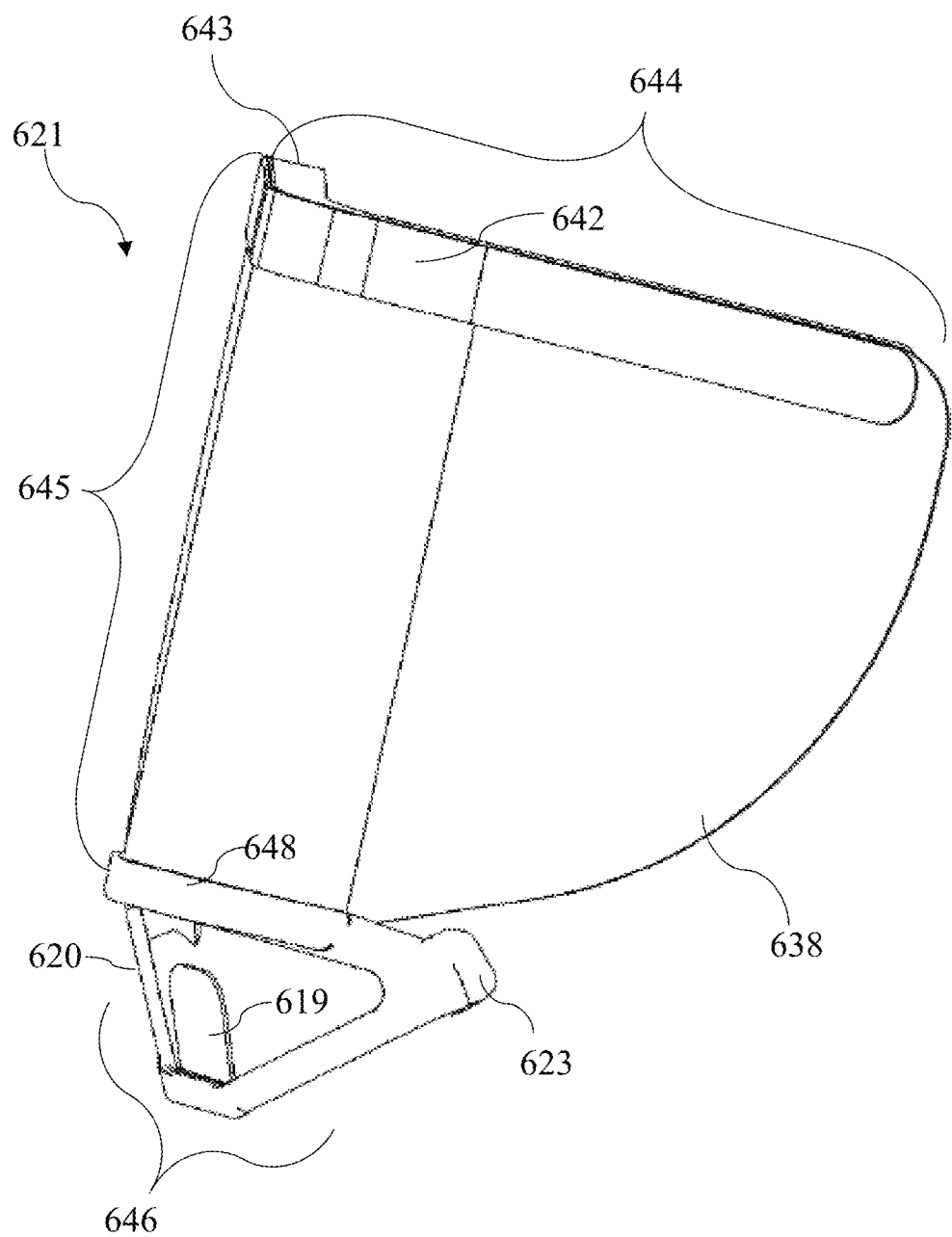
FIG. 8 is a side perspective view of an eye shield assembly.

FIG. 8 is a side perspective view of shield 638. In some embodiments, shield 638 includes conformal headband 642 and/or conformal contact element 643 capable of conforming to a wearer's head.

In at least some embodiments, shield 638 can have, among other things, upper area 644, side area 645 and lower area 646. In certain embodiments, lower area 646 of shield 638 is permanently or removably attached to clip-on element 620.

In at least some embodiments, shield 638 includes conformal headband 642 disposed upon upper area 644 of shield 638. In some embodiments, conformal contact element 643 is disposed upon upper area 644 of shield 638.

In at least some embodiments, shield 638 can be translucent, clear, and/or partial or fully shaded. In certain embodiments, shield 638 can be constructed of various material including but not limited to, polycarbonates and acrylics with varying flexibility.

In at least some embodiments, conformal headband 642 and/or conformal contact element 643 can be placed at other locations on shield 638. In certain embodiments, conformal headband 642 and/or conformal contact element 643 can be continuous and/or intermittently placed on shield 638, they can be integral with shield 638 and/or affixed upon shield 638.

In at least some embodiments, conformal headband 642 materials can be, including but not limited to, a bendable element of aluminum and/or flexible form retaining plastics/foams.

In certain embodiments, conformal contact element 634 can be made of, including but not limited to, adhesive backed foams, elastomers, polymers, flexible and/or air-filled structures.

In at least some embodiments, clip-on element 620 can have, at least one attachment element 623, at least one shield receiving portion 648 and/or at least one adjustable element 619. In certain embodiments, attachment elements 623 can be, among other things, clip tabs and/or snap-in clips.

In at least some embodiments, shield receiving portion 648 can be, among other things, tongue in groove, hook and loop, magnetic and/or adhesive methods. In certain embodiments, adjustable element 619 can be, among other things, an adjustable leaf spring tab, an adjustable biasing tab, incremental tooth connecting tab, and/or shape memory alloys that can be configured to bias toward the user's face.

Adjustable element 619 can be made of, among other things, stainless steel with properties of spring steel, plastics and other metals capable of being bent to retain a configuration that will bias shield assembly 621 toward the wearer. In at least some embodiments, shield 638 protects the forehead region of the wearer by conformal headband 642 and/or contact element 643.

Strap Adjustment Assembly

Figure 9:
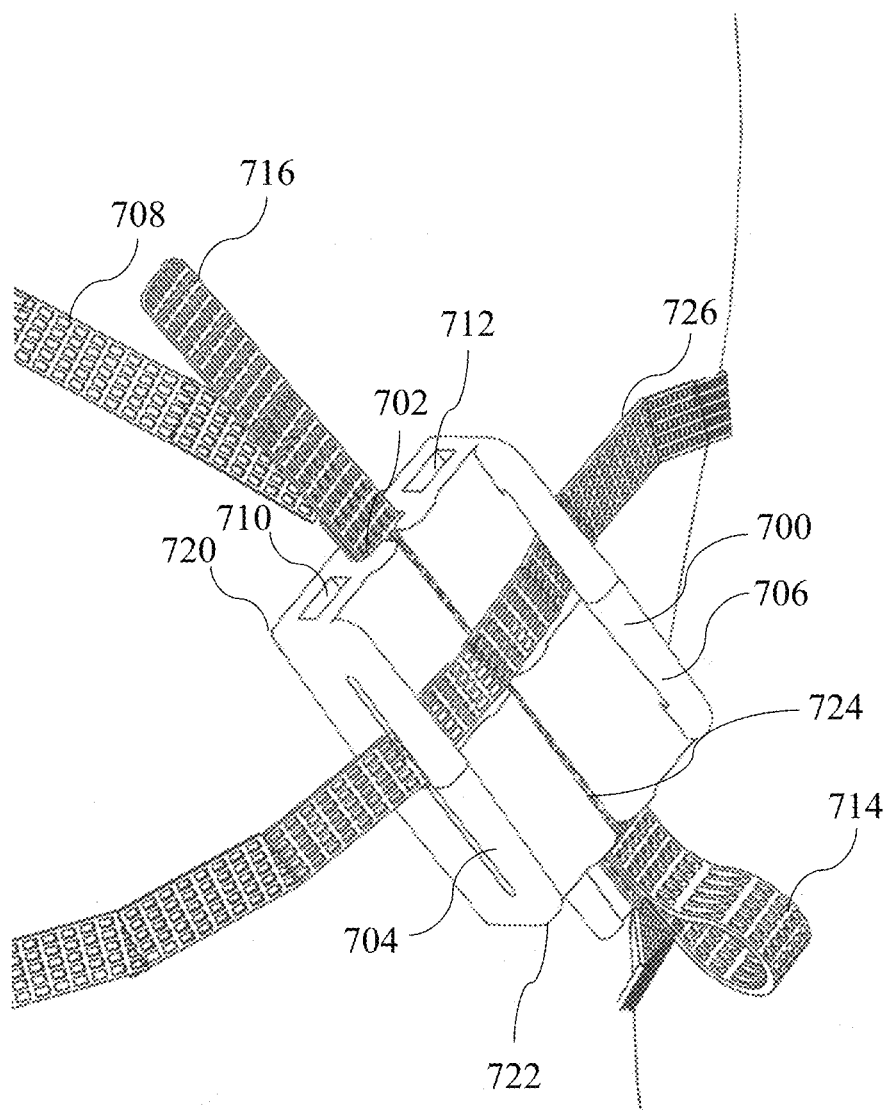
FIG. 9 is a close-up view of a strap adjusted within a strap adjustment frame.

Turning to FIG. 9, strap adjustment frame 700 is shown at the back of the head of a wearer with a continuous strap snapped into the snap-in slots in front of the nose and below the chin. In some embodiments, strap adjustment frame 700 can have at least one hollow strap slot 702 that extends the length of the frame, from side 720 to side 722, and holding bars 704 and 706. Strap adjustment frame 700 can be one continuous piece or multiple pieces configured to snap together. In some embodiments, frame 700 can have additional slots 710 and 712 that extend the length of the frame. Slots in strap adjustment frame 700 can be used to thread and secure strap 708. In some embodiments, slot 702 can be used to adjust the tension of strap 708.

Figure 10:
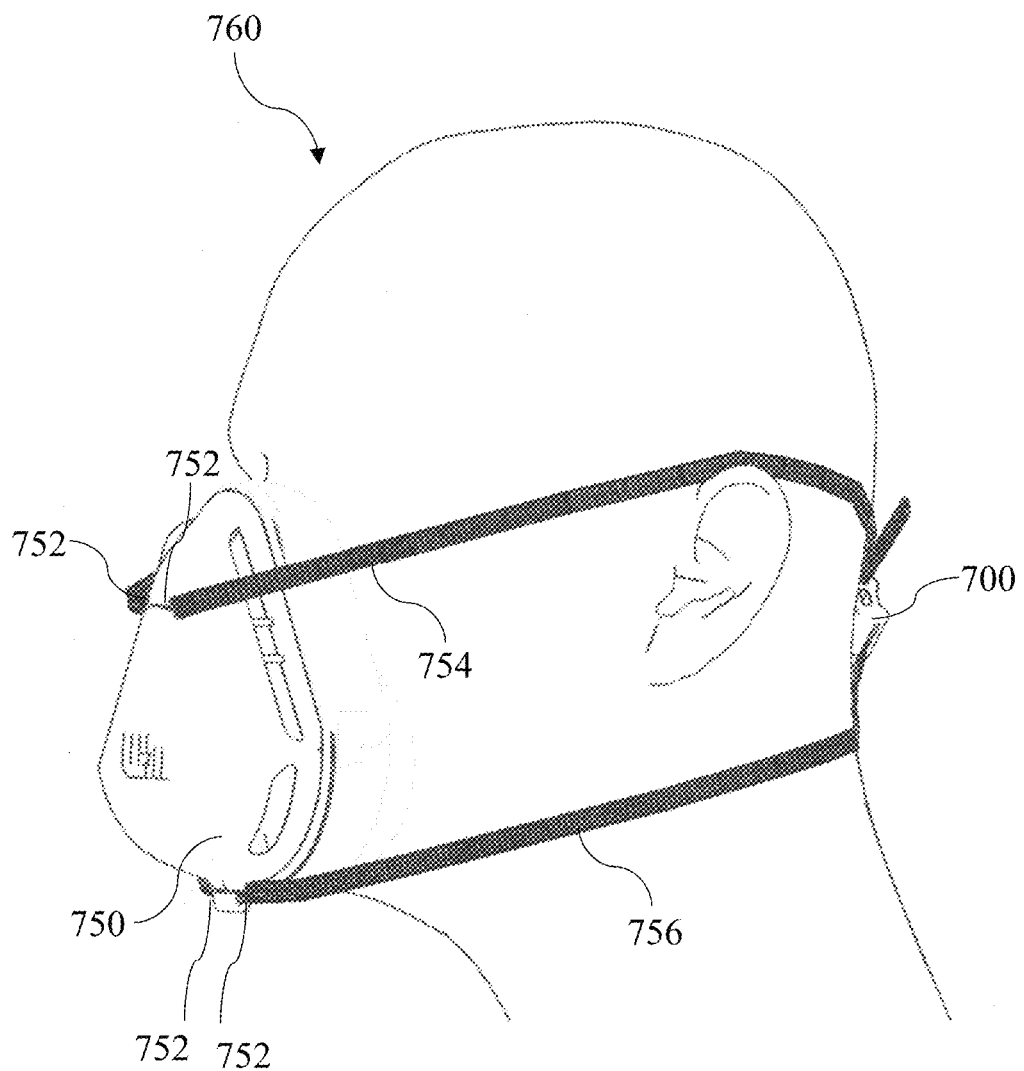
FIG. 10 is a side perspective view of a strap adjustment assembly snapped into a mask mounted on a user.
Figure 11:
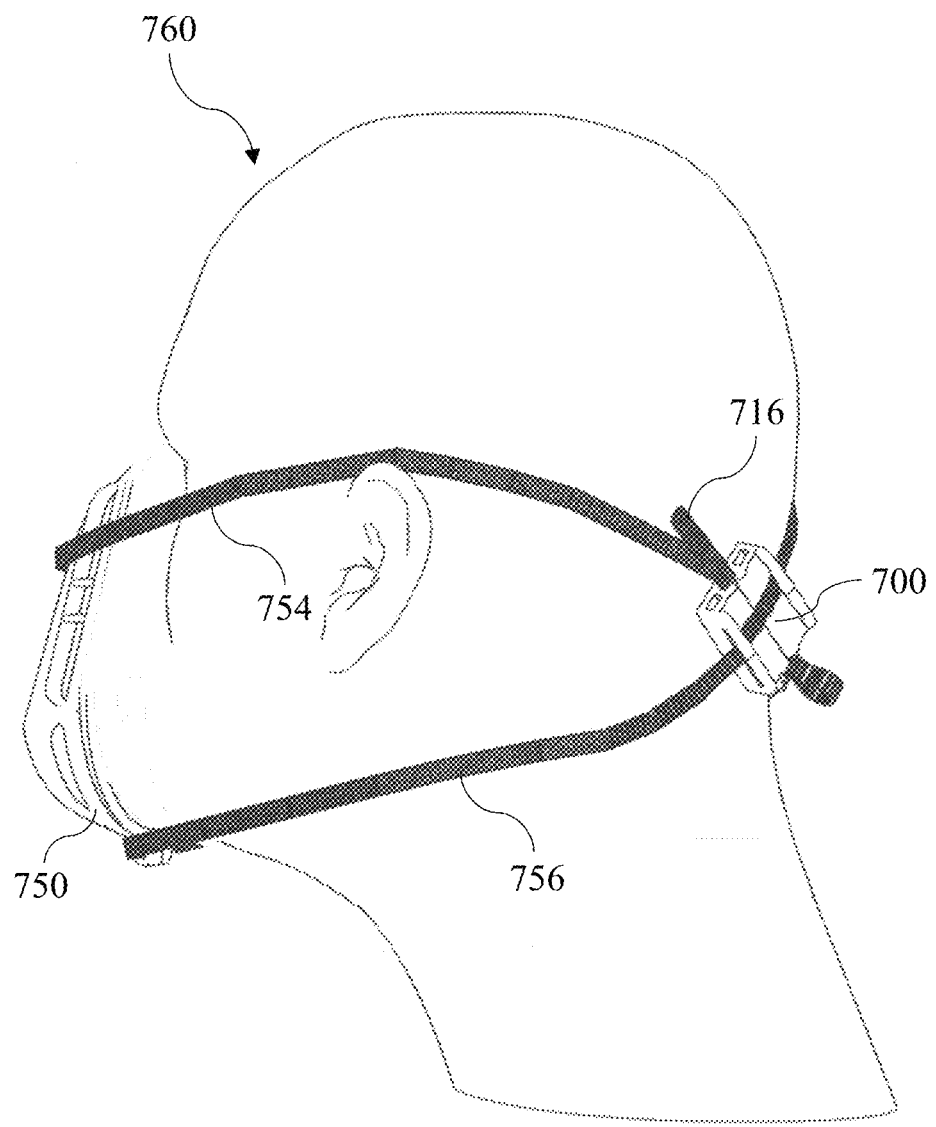
FIG. 11 is a back-perspective view of a strap adjustment assembly snapped into a mask mounted on a user.

Slot 702 can function to thread, secure and adjust a strap or straps. As shown in FIGS. 9-11, strap 708 can be inserted into slot 702 on side 720 of frame 700 and extended through frame 700 such that the strap exits the side 722 of the frame. In some embodiments, strap 708 can then be folded on itself to create pull loop 714. End 716 of strap 708 can then be reinserted into slot 702 on side 722 of frame and extended through the frame such that end 716 exits slot 702 on side 722 of the frame. End 716 and pull loop 714 can then be used to tighten, loosen or otherwise adjust the fit of a mask held in place by the strap adjustment frame.

In some embodiments, frame 700 can include gap 724 that extends the length of the frame and is centered over and continuous with slot 702.

In some embodiments, holding bars 704 and 706 function to thread and secure strap 726 that extends from the opposite side of a wearer's head. In some embodiments, strap 726 is continuous with strap 708. In some embodiments, strap 708 and crossing strap 726 are independent straps.

As shown in FIGS. 10 and 11, strap adjustment assembly 760 can be used to secure mask 750 to the head of a wearer by snap-in slots 752 present on the upper and lower portion of mask 750. Snap-in slots 752 secure straps 754 and 756 that extend from mask 750 to frame 700. In some embodiments, strap 754 and strap 756 are separate, independent straps. In some embodiments, strap 754 is continuous with strap 756.

In some embodiments, strap adjustment assembly 760 can secure a mask or respirator to a user by positioning a strap or straps above the ears and across the jawline and upper neck.

In some or the same embodiments, the strap and mask tension settings established by strap slot 702 and holding bars 704 and 706 can be locked into the strap adjustment frame 700 such that the tension settings are maintained upon removal of strap adjustment frame 700 from a wearer. In some embodiments, this prevents a wearer from having to adjust the frame, straps or attached mask with each use. In some embodiments, the use of snap-in slots 752 on front of the mask 750 allows for the mask to naturally center to the face of a wearer at every use.

In some embodiments, strap adjustment assembly 760 allows the strap to be pulled on or secured in such a manner that the mask or respirator is equally tensioned and centered on a wearer without adjustment to the straps.

In some embodiments, the strap adjustment assembly 760 frame can be a universal device capable of securing a mask or respirator to both adults and children.

In at least some embodiments, strap adjustment assembly 760 is configured to be used with at least the five National Institute for Occupational Safety and Health (NIOSH) certification adult head forms; small, short-wide, large, medium, and long-narrow.

In some embodiments, the strap adjustment assembly 760 minimizes, or at least reduces, the contact between of a strap with the face and head to prevent, or at least reduce the likeliness of, the strap from retaining pollutants, odors and pathogens that can be absorbed from a wearer's sweat and skin.

In some embodiments, strap adjustment assembly can secure a strap made of conventional elastic materials including but not limited to thermoplastic polyurethane, rubber, latex, silicone or nylon. In some embodiments, the strap can have an additional coating to prevent, or at least reduce skin irritation and/or pulling at the hair of a wearer.

In some embodiments, the strap adjustment assembly can be boiled/autoclaved and is reusable. In some embodiments, the strap adjustment assembly can be cleaned by chemical disinfectant methods. In some embodiments, the strap adjustment system does not need to be disassembled from straps to be boiled, autoclaved and/or treated with a chemical disinfectant. In some embodiments where the strap adjustment assembly is used with variations or combination of mask assembly 100, mask assembly 600, mask 101 and/or shield assembly 621, it does not to be disassembled from these devices before being boiled, autoclaved or treated with a chemical disinfectant.

It would be recognized that, particular elements (such as, but not limited to, the clip-on shield assembly and the strap adjustment device) can be incorporated into facemask assemblies in other suitable combinations or arrangements, for example to suit particular applications.

Particular elements (such as, but not limited to, the mask assembly, test scissors, shield assembly, strap adjustment assembly and the like) can be made with, including but not limited to, elastomers, polymers, polyolefins, antistatics, antimicrobials, and repellants.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. A seal test scissor assembly comprising:
   (a) a first scissor frame;
   (b) a second scissor frame;
   (c) a fulcrum point; and
   (d) a biasing mechanism;
   wherein when said seal test scissor assembly is in a closed position, said biasing mechanism is in a relaxed state;

wherein said seal test scissor assembly is configured to be used with a mask assembly.

2. The seal test scissor assembly of claim 1 further comprising:
(e) an attachment point disposed about said first and second scissor frame.

3. The seal test scissor assembly of claim 1 further comprising:
(e) a top portion disposed about said first scissor frame and said second scissor frame, wherein said top portion has a sealing section made of a sealing material.

4. The seal test scissor assembly of claim 3 wherein said sealing material is at least partially disposed about said top portion of said first and second scissor frame.

5. The seal test scissor assembly of claim 3 wherein said sealing material is a foam.

6. The seal test scissor assembly of claim 1 further comprising:
(e) a bottom portion disposed about said first and second scissor frame.

7. The seal test scissor assembly of claim 1 wherein said mask assembly comprises:
(i) a front section;
(ii) a vent system;
(iii) a primary seal;
(iv) a secondary seal; and
(v) a tertiary seal;
wherein said tertiary seal is disposed about said primary seal and is configured to encompass said secondary seal.

8. The seal test scissor assembly of claim 7, wherein said seal test scissor assembly is configured to block said vent system when in a closed position with a sealing section.

9. The seal test scissor assembly of claim 7 further comprising:
(e) a filter.

10. The seal test scissor assembly of claim 9 wherein said filter is pleated.

11. The seal test scissor assembly of claim 7 wherein said secondary seal forms a chin cup.

12. The seal test scissor assembly of claim 7 wherein said tertiary seal is configured to extend outwardly from said primary seal.

13. The seal test scissor assembly of claim 7 wherein said primary seal is made of silicone.

14. The seal test scissor assembly of claim 7 wherein said biasing mechanism is a spring.

15. The seal test scissor assembly of claim 7 wherein said biasing mechanism is a pair of magnets.

16. The seal test scissor assembly of claim 7 wherein said biasing mechanism comprises a spring memory alloy.

17. The seal test scissor assembly of claim 1 wherein said mask assembly comprises:
(i) a front section; and
(ii) a vent system;
wherein said seal test scissor assembly is configured to block said vent system when in a closed position with a sealing section.

* * * * *